United States Patent [19]

Hioki et al.

[11] Patent Number: 5,136,054
[45] Date of Patent: Aug. 4, 1992

[54] SULFONE-CONTAINING AZAMETHINE COMPOUNDS

[75] Inventors: Takeshi Hioki, Osaka; Kiyoteru Kojima, Kobe; Jun Tomioka, Ibaraki, all of Japan

[73] Assignee: Sumitomo Chemical Company, Limited, Osaka, Japan

[21] Appl. No.: 684,290

[22] Filed: Apr. 12, 1990

Related U.S. Application Data

[62] Division of Ser. No. 179,251, Apr. 8, 1988, Pat. No. 5,028,708.

[30] Foreign Application Priority Data

Apr. 14, 1987 [JP] Japan .................................. 62-91146
Jan. 21, 1988 [JP] Japan .................................. 63-11078

[51] Int. Cl.[5] .......................................... C07D 333/68
[52] U.S. Cl. ........................................ 549/53; 544/163; 546/101; 546/166; 546/171; 548/191; 548/442; 558/426
[58] Field of Search ........................................ 549/53

[56] References Cited

U.S. PATENT DOCUMENTS 3,765,882 10/1973 Virkhaus ................................. 549/53
4,281,115  7/1981 Baumann ................................. 549/53
4,460,665  7/1984 Kunikane et al. ....................... 428/199

OTHER PUBLICATIONS

Bello et al. "Near-Infrared Absorbing Methine Dyes", Journal of the Chemical Society, Perkin Trasactions II pp. 815-818 (1987).
Chemical Abstracts, vol. 102, No. 8, Feb. 25, 1985, p. 550.
Chemical Abstracts, vol. 100, No. 24, Jun. 11, 1984, p. 588.
Chemical Abstracts vol. 104, No. 8, Feb. 24, 1986, No. 59741m.

*Primary Examiner*—C. Warren Ivy
*Assistant Examiner*—James H. Turnipseed
*Attorney, Agent, or Firm*—Stevens, Davis, Miller & Mosher

[57] ABSTRACT

This invention provides azamethine compounds represented by the formula (I):

(wherein X represents (Abstract continued on next page.)

-continued

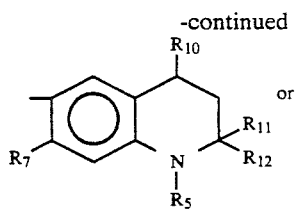

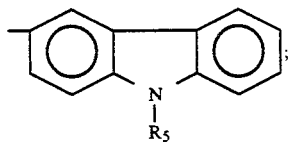

Y represents C=O, C=C(CN)$_2$ or SO$_2$; R$_1$ to R$_4$ represent independently a hydrogen atom, an alkyl group which may be substituted, an alkoxyl group which may be substituted, a halogen atom, a nitro group, a cyano group, a hydroxyl group, an amino group which may be substituted, —A—R or

R$_5$ and R$_6$ represent independently a hydrogen atom, an alkyl group which may be substituted, an aryl group which may be substituted or a cyclohexyl group; R$_5$ and R$_6$ may be combined to form a ring or may form a ring with a hetero atom; R$_7$ and R$_8$ represent independently a hydrogen atom, an alkyl group which may be substituted, an alkoxyl group which may be substituted, a hydroxyl group, a halogen atom, a nitro group, a cyano group, —A—R or

wherein —A represents

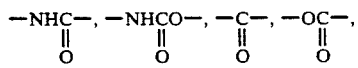

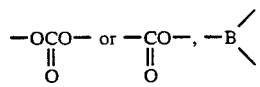

represents

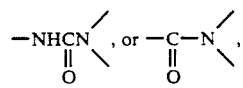

and R and R′ represent independently a hydrogen atom, an alkyl group which may be substituted, an aryl group which may be substituted, a heterocyclic group or a cyclohexyl group; R$_9$ represents a hydrogen atom, an alkyl group which may be substituted, or an aryl or heteroaryl group which may be substituted; and R$_{10}$ to R$_{12}$ represent independently a hydrogen atom or an alkyl group), a process for producing such compounds, and a medium for recording optical information using these compounds.

3 Claims, 10 Drawing Sheets

SULFONE-CONTAINING AZAMETHINE COMPOUNDS

This is a division of application Ser. No. 179,251 filed Apr. 8, 1988 now U.S. Pat. No. 5,028,708.

This invention relates to azamethine compounds, a process for preparing the same, and a medium for recording optical information using such compounds.

The compounds of this invention find their use not only for a medium for recording optical information mentioned above but also for various other electrochemical devices including fine-color separation filter for color image pickup devices and color displays, sharp cut filters for an infrared ray sensor, photoconductive organic compositions, dye laser, etc.

The optical information recording media, for which the use of the compounds of this invention is especially envisaged, have a prominent feature that they suffer from no wear trouble because of the structural peculiarity that the medium itself is not contacted with the writing and reading head. In view of such and other advantages, many studies have been made for the development of various types of optical information media.

Among these optical information recording media, the so-called heat mode optical information recording medium is attracting attention and ardent studies are being made on this type of optical information recording medium as this recording medium unncessitates the developing treatment in a dark place. This heat mode optical recording medium is a type of optical information recording medium which utilizes recording light as heat source. As a typical example of such heat mode optical recording medium, there is known a pit-forming type in which the medium is partly melted and removed by recording light such as laser to form the small holes called pits for recording information and these pits are detected by reading light for read out of recorded information.

Thus, the optical information recording media are required to be able to absorb energy of laser light at high efficiency, for which it is necessary that said media have high absorptivity of laser light of specific wavelengths used for recording and that they also have a high reflectance for laser light of specific wavelengths used for regeneration of information for allowing correct regeneration of information.

In most of such pit-forming type recording media, especially those using semiconductor laser as light source with which a dimensional reduction of the apparatus was possible, a material mainly composed of Te has been used for the recording layer.

Recently, however, because of the problem of environmental pollution involved in use of such Te-based material and also in view of the necessity for higher sensitivity and lower production cost, many proposals and reports have been made on the recording media using a recording layer made of an organic material mainly composed of an organic dye instead of a Te-based material.

As the dyes usable for such organic material, there have been proposed cyanine dyes (see, for example, Japanese Patent Application Kokai (Laid-Open) No. 114989/83), metal complex dyes (see, for example, Japanese Patent Application Kokai (Laid-Open) No. 16888/83), etc.

These compounds, however, are unstable for storage in the air and for light in a thin film. Various method for stabilization thereof have been proposed (as for instance in Japanese Patent Application Kokai (Laid-Open) No. 55794/84), and efforts for further improvement are still being made.

The present invention is intended to provide a medium for recording optical information which has high absorptivity and reflectivity of semiconductor laser light and is also stable to light and heat.

As a result of assiduous studies for improving said defects of the conventional materials for optical recording media, the present inventors found that the azamethine compounds represented by the following general formula (I) are stable and especially useful as a recording material, and the present invention was achieved on the basis of such finding.

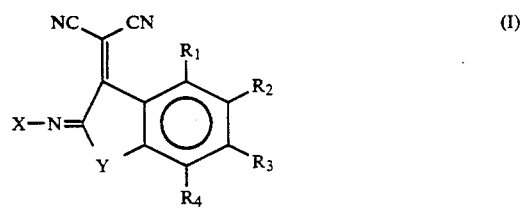

(wherein X represents

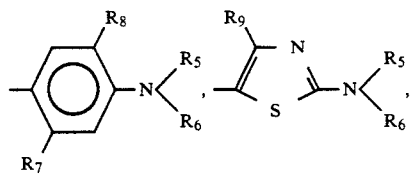

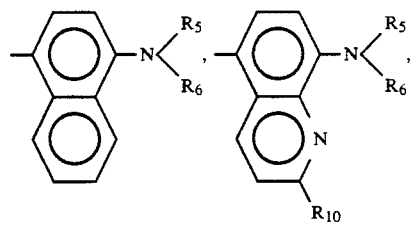

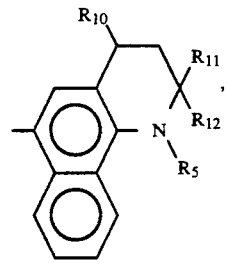

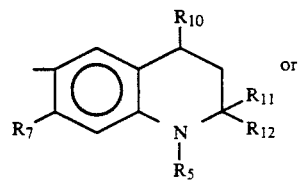

or

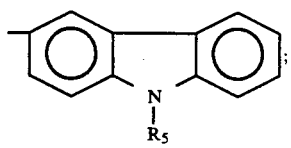

Y represents C=O, C=C(CN)$_2$ or SO$_2$; R$_1$ to R$_4$ represent independently a hydrogen atom, an alkyl group which may be substituted, an alkoxyl group which may be substituted, a halogen atom, a nitro group, a cyano group, a hydroxyl group, an amino group which may be substituted, —A—R or

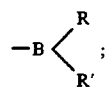

R$_5$ and R$_6$ represent independently a hydrogen atom, an alkyl group which may be substituted, an aryl group which may be substituted or a cyclohexyl group; R$_5$ and R$_6$ may be combined to form a ring or may form a ring with a hetero atom; R$_7$ and R$_8$ represent independently a hydrogen atom, an alkyl group which may be substituted, an alkoxyl group which may be substituted, a hydroxyl group, a halogen atom, a nitro group, a cyano group, —A—R or

wherein —A represents

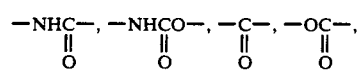

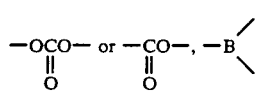

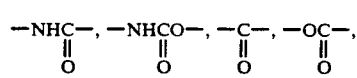

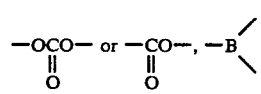

represents

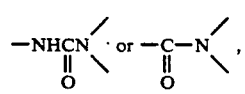

and R and R' represent independently a hydrogen atom, an alkyl group which may be substituted, an aryl group which may be substituted, a heterocyclic residue or a cyclohexyl group; R$_9$ represents a hydrogen atom, an alkyl group which may be substituted, or an aryl or heteroaryl group which may be substituted; and R$_{10}$ to R$_{12}$ represent independently a hydrogen atom or an alkyl group, with the proviso that X represents

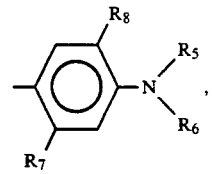

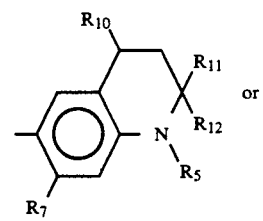

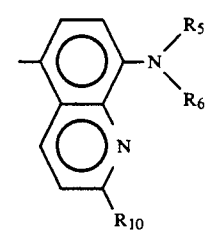

(wherein R$_5$ and R$_6$ represent independently a hydrogen atom, an alkyl group which may be substituted, an aryl group which may be substituted or a cyclohexyl group; R$_5$ and R$_6$ may be combined to form a ring or may form a ring with a hetero atom; R$_7$ represents an alkyl group which may be substituted, an alkoxyl group which may be substituted, a hydroxyl group, a halogen atom or

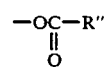

wherein R" represents an alkyl group which may be substituted; R$_8$ represents a hydrogen atom, an alkyl group which may be substituted, an alkoxyl group which may be substituted or a halogen atom; and R$_{10}$ to R$_{12}$ represent independently a hydrogen atom or an alkyl group), when Y represents C=C(CN)$_2$.).

More specifically, the present inventors found that the azamethine compounds represented by the following formula (II) are excellent in stability and more useful as a recording material:

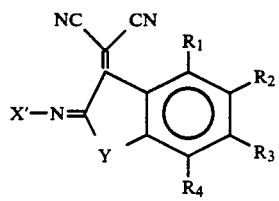

wherein Y represents C=O, C=C(CN)$_2$ or SO$_2$; R$_1$ to R$_4$ are as defined above; and X' represents

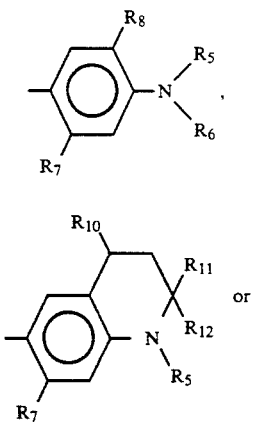

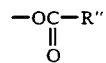

(wherein $R_5$ and $R_6$ represent independently a hydrogen atom, an alkyl group which may be substituted, an aryl group which may be substituted or a cyclohexyl group; $R_5$ and $R_6$ may be combined to form a ring or may form a ring with a hetero atom; $R_7$ represents an alkyl group which may be substituted, an alkoxyl group which may be substituted, a hydroxyl group, a halogen atom or $$-OC-R''$$
$$\phantom{-O}\|$$
$$\phantom{-OC-}O$$

wherein $R''$ represents an alkyl group which may be substituted; $R_8$ represents a hydrogen atom, an alkyl group which may be substituted, an alkoxyl group which may be substituted or a halogen atom; and $R_{10}$ to $R_{12}$ represent independently a hydrogen atom or an alkyl group).

Among the compounds represented by the above-shown formula (II), the following are especially preferred:

the azamethine compounds of formula (II) wherein Y is C=O or C=C(CN)$_2$;

the azamethine compound of formula (II) wherein $R_7$ is an alkyl group which may be substituted or an alkoxyl group which may be substituted;

the azamethine compounds of formula (II) wherein Y is C=O and $R_7$ is an alkyl group which may be substituted; and the azamethine compounds of formula (II) wherein Y is C=C(CN)$_2$ and $R_7$ is an alkoxyl group which may be substituted.

The compounds represented by the formula (I) according to this invention can be produced by condensing the compounds represented by formula (III):

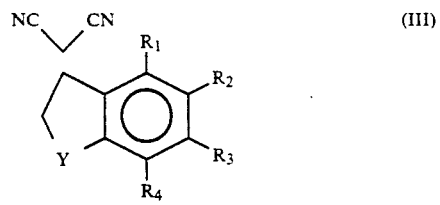

(wherein Y represents C=O, C=C(CN)$_2$ or SO$_2$; $R_1$ to $R_4$ represent independently a hydrogen atom, an alkyl group which may be substituted, an alkoxyl group which may be substituted, a halogen atom, a nitro group, a cyano group, a hydroxyl group, an amino group which may be substituted, —A—R or

wherein —A— represents

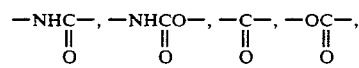

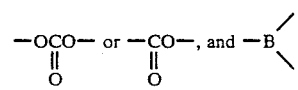

represents

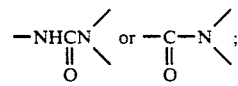

and R and R' represent independently a hydrogen atom, an alkyl group which may be substituted, an aryl group which may be substituted, a heterocyclic residue or a cyclohexyl group) and the compounds represented by formula (IV):

$$X-N=O \qquad (IV)$$

(wherein X represents

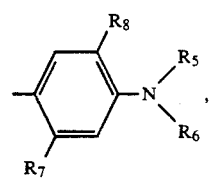

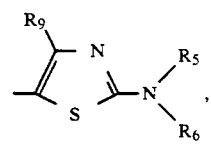

-continued

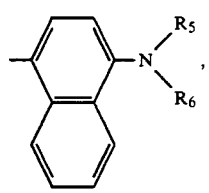

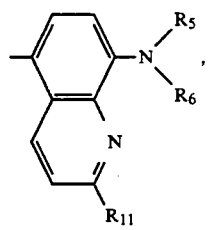

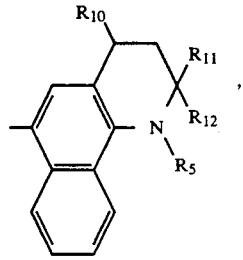

or

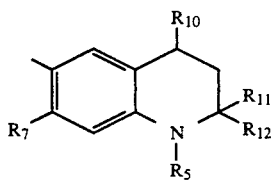

or

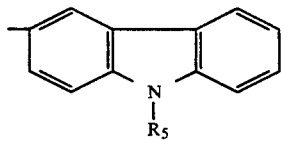

wherein $R_5$ and $R_6$ represent independently a hydrogen atom, an alkyl group which may be substituted, an aryl group which may be substituted or a cyclohexyl group; $R_5$ and $R_6$ may be combined to form a ring or may form a ring with a hetero atom; $R_7$ and $R_8$ represent independently a hydrogen atom, an alkyl group which may be substituted, an alkoxyl group which may be substituted, a hydroxyl group, a halogen atom, a nitro group, a cyano group, —A—R or

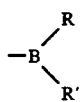

wherein —A— represents

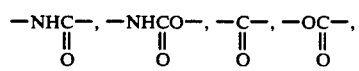

-continued

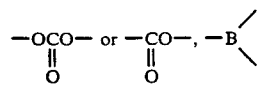

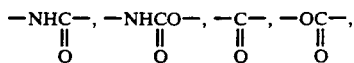

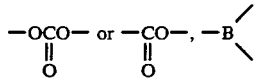

represents

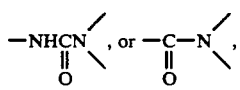

and R and R' represent independently a hydrogen atom, an alkyl group which may be substituted, an aryl group which may be substituted, a heterocyclic residue or a cyclohexyl group; $R_9$ represents a hydrogen atom, an alkyl group which may be substituted, or an aryl or heteroaryl group which may be substituted; and $R_{10}$ to $R_{12}$ represent independently a hydrogen atom or an alkyl group, with the proviso that X represents

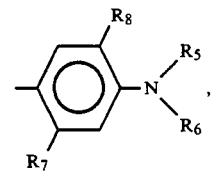

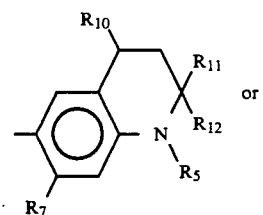

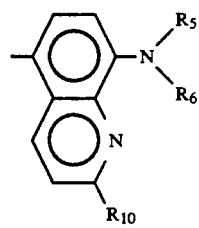

(wherein $R_5$ and $R_6$ represent independently a hydrogen atom, an alkyl group which may be substituted, an aryl group which may be substituted or a cyclohexyl group; $R_5$ and $R_6$ may be combined to form a ring or may form a ring with a hetero atom; $R_7$ represents an alkyl group which may be substituted, an alkoxyl group which may be substituted, a hydroxyl group, a halogen atom or

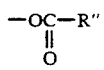

wherein R" represents an alkyl group which may be substituted; $R_8$ represents a hydrogen atom, an alkyl group which may be substituted, an alkoxyl group which may be substituted or a halogen atom; and $R_{10}$ to $R_{12}$ represent independently a hydrogen atom or an alkyl group), when Y represents $C=C(CN)_2$.).

Said condensation reaction is carried out by using an inert organic solvent such as methanol, ethanol, n-propanol, acetic acid, toluene, chlorobenzene, chloroform, dimethylformamide, N-methylpyrrolidone, dimethyl sulfoxide, sulforan, acetonitrile, acetic anhydride and the like.

A compound of formula (III) and a compound of formula (IV) are mixed in an inert organic solvent such as mentioned above, further added with a catalyst such as preferably piperidine, pyridine, triethylamine or an organic base such as a mixture of piperidine and glacial acetic acid and reacted at 0°~100° C., preferably 20°~80° C. for 0.5~10 hours, preferably 1~5 hours. The reaction mixture is cooled and filtered to give the crude cakes of a compound of this invention represented by the formula (I). Such crude cakes may be purified by recrystallization from a proper solvent or by other means.

The structures of the optical information recording media using an azamethine compound of this invention and the transmittance and reflectance spectra of such recording media measured by irradiating the media via the substrate are shown in the accompanying drawings in which.

Figure 1:
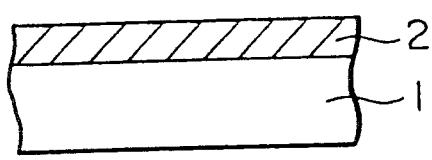
FIGS. 1 to 4 are the sectional views showing the structures of the optical information recording media according to this invention. In the drawing, reference numeral 1 indicates a substrate, 2 a recording layer, 3 an underlayer, and 4 a protective layer.
Figure 2:
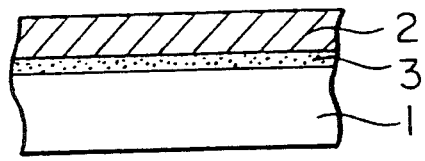
Figure 3:
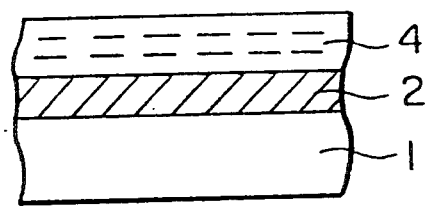
Figure 4:
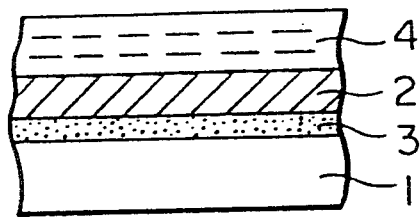

The optical information recording media using an azamethine compound obtained according to the process of this invention have the basic structure shown in FIG. 1, and where necessary an underlayer and/or a protective layer may be further provided as shown in FIGS. 2 to 4. Two pieces of recording medium having the same structure may be combined so that the recording layers 2 of the respective recording media will be positioned on the inside facing each other to form a so-called air sandwich structure. Also, two pieces of recording medium may be bonded to each other with a protective layer 4 interposed therebetween. In these recording media, recording of information is made by the shape changes of the membrane caused by the thermal action of laser light, and the regeneration of information is made by detecting the difference between reflected light from the section which had a shape change and that from the section with no shape change.

Formation of the recording layer may be accomplished by ordinary means such as vacuum deposition or solution coating. The recording layer may be formed by using one or a mixture of two or more of the dyes of this invention. Also, the dye(s) of this invention may be used in combination with other dye(s), in the form of mixture, laminate, etc. The dyes of this invention may be used by mixing or dispersing them in a high-molecular material such as silicone, polyamide resin, vinyl resin, natural polymers, etc., or other materials such as silicone coupling agent. Also, they may be used with a stabilizer, dispersing agent, antistatic agent and the like.

The thickness of the recording layer in the recording media of this invention is in the range of 50 to 5,000 Å, preferably 100 to 2,000 Å.

The substrate material used in this invention is to one which is transparent to laser beams. Examples of such material are glass, quartz, and various types of plastic such as polycarbonate resin, vinyl chloride resin, polymethyl methacrylate resin (PMMA), polyester resin, polyethylene resin, polypropylene resin, polyamide resin, polystyrene resin, epoxy resin, and other mono- and copolymers.

Underlayer 3 is provided for the purposes of protecting the substrate from the solvent, improving adhesiveness, forming a pregroove, etc. Said high-molecular materials, silane coupling agent, inorganic compounds ($SiO_2$, $MgF_2$, ZnO, etc.), ultraviolet-cured resins, thermosetting resins and the like can be used as the underlayer material.

The thickness of such underlayer is in the range of 0.1 to 30 μm, preferably 0.2 to 10 μm.

Protective layer 4 is provided for protecting the substrate from dirt and dust and improving the chemical stability of the recording layer.

The thickness of such protective layer should be not less than 0.1 μm, preferably not less than 50 μm.

The films of the novel azamethine compounds according to this invention show the absorption maximum in the wavelength region of 600 to 850 nm, have a high reflectance in the region of 600 to 900 nm and are also very stable, so that the films of said compounds of this invention find a wide scope of uses and are particularly useful as a medium for recording optical information.

The present invention will hereinafter be described more in detail with reference to the examples thereof, but it is to be understood that these examples are merely intended to be illustrative and not to be construed as limiting the scope of the invention.

In the Examples shown below, the measurement of the spectrum was made by irradiating the medium via the substrate by using a spectrophotometer Model UV-365 mfd. by Shimazu Seisakusho Co., Ltd. The measurment of thickness was made by using a film thickness gauge Talystep mfd. by Taylor & Hobson Inc.

EXAMPLE 1

0.50 g of the compound of formula (1):

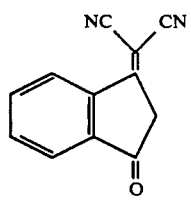 (1)

and 0.94 g of the compound of formula (2):

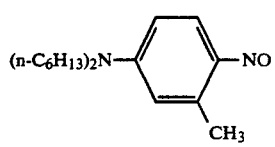 (2)

where mixed in 10 ml of methanol. The solution was added with 0.2 g of piperidine, stirred at 40° C. for 2 hours and then cooled to 5° C. The mixed solution was filtered, washed with ice-cold methanol and dried. The resulting product was recrystallized from chloroform to obtain 0.87 of purified cakes of the compound of the following formula (3). Yield: 70.3%. Melting point: 228°~230° C. Absorbance in acetone solution: $\lambda max = 701$ nm, $\xi = 3.23 \times 10^4$.

NMR in CDCl$_3$: 0.92 ppm (6H), 1.35 ppm (12H), 1.68 ppm (4H), 2.66 ppm (3H), 3.43 ppm (4H), 6.50 ppm (1H), 6.57 ppm (1H), 7.70 ppm (2H), 7.85 ppm (2H), 8.62 ppm (1H).

EXAMPLE 2

1.00 g of the compound of formula (4):

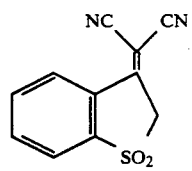 (4)

and 1.69 g of the compound of formula (5):

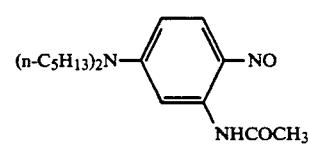 (5)

were mixed in 20 ml of methanol, followed by addition of 0.5 g of piperidine. The mixed solution was stirred at 50° C. for 2 hours and then cooled to 5° C. The mixed solution was filtered, washed with ice-cold methanol and dried. The resulting product was recrystallized from chloroform to obtain 1.42 g of purified cakes of the compound of the following formula (6). Yield: 61.0%.

Melting point: 164°~164.5° C.

Absorbance in acetone solution: $\lambda max = 674$ nm; $\xi = 6.14 \times 10^4$.

NMR in CDCl$_3$: 0.94 ppm (6H), 1.37 ppm (8H), 1.72 ppm (4H), 2.32 ppm (3H), 3.50 ppm (4H), 6.58 ppm (1H), 7.82 ppm (1H), 7.93 ppm (2H), 8.12 ppm (1H), 8.25 ppm (1H), 8.87 ppm (1H), 9.70 ppm (1H).

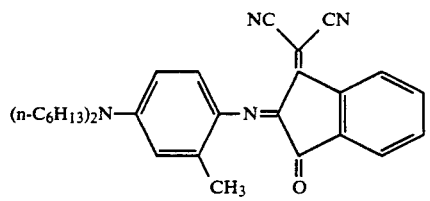 (3)

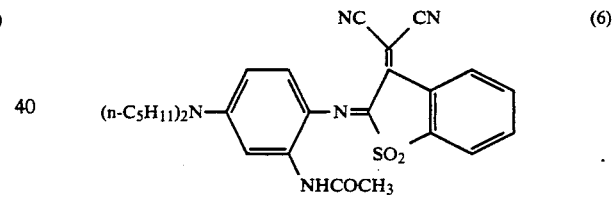 (6)

The compounds shown in Table 1 below were produced in the same way as Example 1 or Example 2.

TABLE 1

General formula:

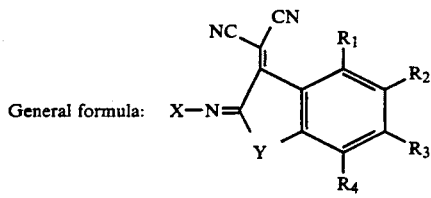

| No. | R$_1$ | R$_2$ | R$_3$ | R$_4$ | Y | X | Absorption maximum wavelength in acetone (nm) |
|---|---|---|---|---|---|---|---|
| 3 | H | H | H | H | C=O |  | 700 |

TABLE 1-continued

General formula:

| No. | R₁ | R₂ | R₃ | R₄ | Y | X | Absorption maximum wavelength in acetone (nm) |
|---|---|---|---|---|---|---|---|
| 4 | H | H | H | H | $\overset{\text{C}}{\underset{\text{O}}{\|}}$ | 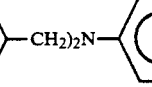 | 702 |
| 5 | H | H | H | H | $\overset{\text{C}}{\underset{\text{O}}{\|}}$ | 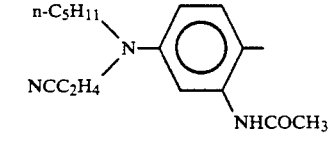 | 685 |
| 6 | H | H | H | H | $\overset{\text{C}}{\underset{\text{O}}{\|}}$ | 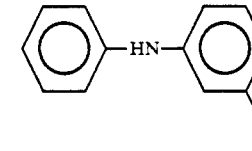 | 700 |
| 7 | H | H | H | H | $\overset{\text{C}}{\underset{\text{O}}{\|}}$ | 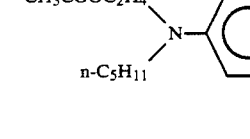 | 709 |
| 8 | H | H | H | H | $\overset{\text{C}}{\underset{\text{O}}{\|}}$ | 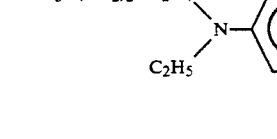 | 708 |
| 9 | H | H | H | H | $\overset{\text{C}}{\underset{\text{O}}{\|}}$ | 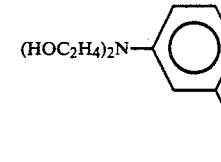 | 701 |
| 10 | H | H | H | H | $\overset{\text{C}}{\underset{\text{O}}{\|}}$ | 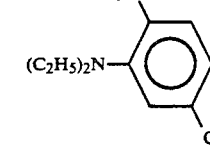 | 720 |
| 11 | H | H | H | H | $\overset{\text{C}}{\underset{\text{O}}{\|}}$ | 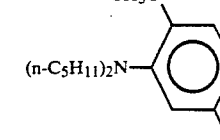 | 721 |

TABLE 1-continued

General formula:

$$X-N\underset{Y}{=}C-C(CN)_2 \text{ attached to benzene ring with } R_1, R_2, R_3, R_4$$

| No. | $R_1$ | $R_2$ | $R_3$ | $R_4$ | Y | X | Absorption maximum wavelength in acetone (nm) |
|---|---|---|---|---|---|---|---|
| 12 | H | H | H | H | C=O | 4-(C$_2$H$_5$)$_2$N-phenyl with CH$_2$-phenyl substituent | 702 |
| 13 | H | H | H | H | C=O | 4-(n-C$_4$H$_9$)$_2$N-phenyl with OH | 660 |
| 14 | H | H | H | H | C=O | N(cyclohexyl)(n-C$_4$H$_9$)-phenyl-Cl | 690 |
| 15 | H | H | H | H | C=O | 4-morpholino-phenyl-OCH$_3$ | 661 |
| 16 | H | H | H | H | C=O | CH$_3$-phenyl-O(CH$_2$)$_2$-N(C$_2$H$_5$)-phenyl-CH$_3$ | 691 |
| 17 | H | H | H | H | C=O | (CH$_3$)$_3$C-CH$_2$-CH(CH$_3$)-phenyl with N(C$_2$H$_5$) and CH$_3$ substituents | 701 |
| 18 | H | H | H | H | C=O | (CH$_3$)$_3$C-CH$_2$-CH(CH$_3$)-phenyl with N(C$_3$H$_7$(i)) and CH$_3$ substituents | 703 |

TABLE 1-continued

General formula:

$$X-N=\underset{Y}{\overset{}{C}}-C(CN)_2=\text{(aryl with } R_1, R_2, R_3, R_4\text{)}$$

| No. | R₁ | R₂ | R₃ | R₄ | Y | X | Absorption maximum wavelength in acetone (nm) |
|-----|----|----|----|----|----|---|-----------------------------------------------|
| 19 | H | H | H | H | C=O | 2,4-dimethylphenyl-N(C₄H₉(n))-C(CH₃)₂-CH₂-CH(CH₃)- | 702 |
| 20 | H | H | H | H | C=O | 2,4-dimethylphenyl-N(C₆H₁₃(n))-C(CH₃)₂-CH₂-CH(CH₃)- | 700 |
| 21 | H | H | H | H | C=O | 4-methylphenyl-N(C₂H₄-C₆H₅)-C(CH₃)₂-CH₂-CH(CH₃)- | 701 |
| 22 | H | H | H | H | C=O | 4-ethylphenyl-N(C₂H₅)-C(CH₃)₂-CH₂-CH(CH₃)- | 704 |
| 23 | H | H | H | H | C=O | 4-methylphenyl-N(C₂H₄OH)-C(CH₃)₂-CH₂-CH(CH₃)- | 702 |

TABLE 1-continued

General formula:

$$X-N=\underset{Y}{\overset{}{C}}-C(CN)_2\text{-Ar}(R_1,R_2,R_3,R_4)$$

| No. | $R_1$ | $R_2$ | $R_3$ | $R_4$ | Y | X | Absorption maximum wavelength in acetone (nm) |
|---|---|---|---|---|---|---|---|
| 24 | H | H | H | H | C=O | 2-[(N-ethyl-N-neopentyl)amino]-5-isopropyl-α-methylbenzyl | 705 |
| 25 | H | H | H | H | C=O | 2-[(N-ethyl-N-neopentyl)amino]-5-methoxy-α-methylbenzyl | 642 |
| 26 | H | H | H | Cl | C=O | 4-(diethylamino)-2-methylphenyl | 713 |
| 27 | H | H | H | H | C=O | 2-[(N-methyl-N-neopentyl)amino]-α-methylbenzyl | 630 |
| 28 | H | H | H | H | C=O | 4-[bis(2-ethoxyethyl)amino]-1-naphthyl | 701 |
| 29 | H | H | H | H | C=O | 4-(di-n-pentylamino)-8-quinolyl | 670 |

TABLE 1-continued
General formula: 
| No. | R₁ | R₂ | R₃ | R₄ | Y | X | Absorption maximum wavelength in acetone (nm) |
|---|---|---|---|---|---|---|---|
| 30 | H | H | H | H | $\overset{\text{C}}{\underset{\text{O}}{\|}}$ | 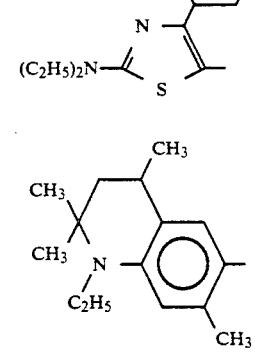 | 731 |
| 31 | H | H | H | Cl | $\overset{\text{C}}{\underset{\text{O}}{\|}}$ | 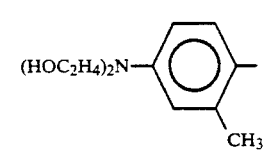 | 713 |
| 32 | H | H | H | Cl | $\overset{\text{C}}{\underset{\text{O}}{\|}}$ | 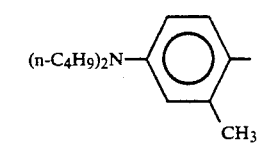 | 710 |
| 33 | H | H | H | Cl | $\overset{\text{C}}{\underset{\text{O}}{\|}}$ | 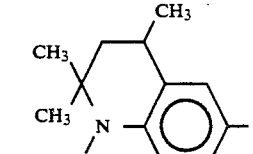 | 714 |
| 34 | H | H | H | Cl | $\overset{\text{C}}{\underset{\text{O}}{\|}}$ | 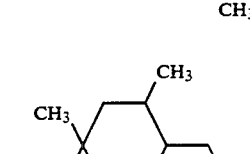 | 715 |
| 35 | H | H | H | Cl | $\overset{\text{C}}{\underset{\text{O}}{\|}}$ |  | 715 |

TABLE 1-continued

General formula:

$$X-N=\underset{Y}{\overset{\underset{\displaystyle NC}{\diagdown}C=\underset{\displaystyle }{\overset{\displaystyle CN}{\diagup}}}{C}}-\underset{}{\overset{}{C_6H_2R_1R_2R_3R_4}}$$

| No. | $R_1$ | $R_2$ | $R_3$ | $R_4$ | Y | X | Absorption maximum wavelength in acetone (nm) |
|---|---|---|---|---|---|---|---|
| 36 | H | H | H | Cl | C=O | 4-[N-(2,2-dimethyl-4-methylpentan-4-yl... see structure: N(CH$_2$CH(CH$_3$)-C(CH$_3$)$_2$-)(C$_2$H$_4$OH) on 2,4-dimethylphenyl | 712 |
| 37 | H | H | Br | H | C=O | 4-CH$_3$O, 2-(n-C$_5$H$_{11}$)$_2$N, 5-NHCOC$_3$H$_7$(n) phenyl | 731 |
| 38 | H | H | NO$_2$ | H | C=O | 4-[N(n-C$_6$H$_{13}$)(C$_2$H$_5$)]-3-CH$_3$-phenyl | 742 |
| 39 | H | H | NO$_2$ | H | C=O | naphthyl with N(CH$_3$)(CH$_2$CH(CH$_3$)C(CH$_3$)$_2$-) substituent | 746 |
| 40 | H | H | CN | H | C=O | 4-[N(n-C$_5$H$_{11}$)(CH$_2$CH$_2$CN)]-3-CH$_3$-, 5-NHCOCH$_3$-phenyl... see structure | 724 |
| 41 | H | H | OCOOC$_2$H$_5$ | H | C=O | 4-(C$_2$H$_5$)$_2$N-3-CH$_3$-phenyl | 685 |
| 42 | H | H | H | CH$_3$ | C=O | 4-(n-C$_5$H$_{11}$)$_2$N-3-CH$_3$-phenyl | 695 |

TABLE 1-continued

General formula: 
$$X-N=\underset{Y}{\overset{}{C}}-C(CN)_2=C\text{-Ar}(R_1, R_2, R_3, R_4)$$

| No. | R₁ | R₂ | R₃ | R₄ | Y | X | Absorption maximum wavelength in acetone (nm) |
|---|---|---|---|---|---|---|---|
| 43 | H | H | COOCH₃ | H | C=O | phenyl-O-(CH₂)₄-N(n-C₆H₁₃)-(phenyl with CH₃, COCH₃) | 720 |
| 44 | H | H | H | CONHC₄H₉(n) | C=O | (C₂H₅)₂N-(phenyl with CH₃) | 723 |
| 45 | H | H | OCH₃ | H | C=O | N(n-C₅H₁₁)(NCC₂H₄)-(phenyl with CH₃, NHCOCH₃) | 698 |
| 46 | H | H | H | H | SO₂ | (C₂H₅)₂N-(phenyl with CH₃, NHCOCH₃) | 675 |
| 47 | H | H | H | H | SO₂ | N(n-C₅H₁₁)(NCC₂H₄)-(phenyl with CH₃, NHCOCH₃) | 650 |
| 48 | H | H | H | H | SO₂ | N(C₂H₅)(CH₃OCOC₂H₄)-(phenyl with CH₃, OCH₃) | 641 |
| 49 | H | H | H | H | SO₂ | N(CH₃O(CH₂)₄)(n-C₅H₁₁)-(phenyl with CH₃, OCOCH₃) | 672 |
| 50 | H | H | H | H | SO₂ | (N-C₆H₁₃)₂N-(phenyl with CH₃, NHSO₂CH₃) | 674 |

TABLE 1-continued

General formula:

$$\underset{Y}{\overset{X-N}{\diagdown}}C=C\underset{\phantom{X}}{\overset{CN}{\diagup}}\phantom{=}\text{(phenyl with }R_1, R_2, R_3, R_4\text{)}$$

| No. | R$_1$ | R$_2$ | R$_3$ | R$_4$ | Y | X | Absorption maximum wavelength in acetone (nm) |
|---|---|---|---|---|---|---|---|
| 51 | H | H | H | H | SO$_2$ | 4-(C$_2$H$_5$)$_2$N-phenyl-3-CH$_3$ | 712 |
| 52 | H | H | H | H | SO$_2$ | 4-(n-C$_4$H$_9$)$_2$N-phenyl-3-CH$_3$ | 715 |
| 53 | H | H | H | H | SO$_2$ | 4-(C$_2$H$_5$)$_2$N-phenyl-3-C$_2$H$_5$ | 712 |
| 54 | H | H | H | H | SO$_2$ | 2-CH$_3$O-4-(C$_2$H$_5$)$_2$N-phenyl-5-CH$_3$ | 725 |
| 55 | H | H | H | H | SO$_2$ | 2-CH$_3$O-4-(HOC$_2$H$_4$)$_2$N-phenyl-5-CH$_3$ | 724 |
| 56 | H | H | H | H | SO$_2$ | N-ethyl carbazolyl | 651 |
| 57 | H | H | H | H | SO$_2$ | 2-(C$_2$H$_5$)$_2$N-4-phenyl-thiazolyl | 702 |

TABLE 1-continued

General formula:

$$X-N=\underset{Y}{\overset{}{C}}-\underset{}{\overset{NC}{\underset{}{C}}=\overset{CN}{\underset{}{C}}}-\underset{R_4}{\overset{R_1}{\underset{R_3}{\overset{R_2}{\text{Ar}}}}}$$

| No. | R₁ | R₂ | R₃ | R₄ | Y | X | Absorption maximum wavelength in acetone (nm) |
|---|---|---|---|---|---|---|---|
| 58 | H | H | H | H | SO₂ | [2-(N,N-dimethylamino-tert-butyl)-4-methylphenyl group with CH(CH₃)-CH₂-C(CH₃)₂-N(CH₃)₂] | 648 |
| 59 | H | H | H | H | SO₂ | [N-ethyl, 4,5-dimethyl analogue with CH(CH₃)-CH₂-C(CH₃)₂-N(CH₃)(C₂H₅)] | 718 |
| 60 | H | H | H | H | SO₂ | [N-n-butyl, 4,5-dimethyl analogue with CH(CH₃)-CH₂-C(CH₃)₂-N(CH₃)(C₄H₉(n))] | 717 |
| 61 | H | H | H | H | SO₂ | [N-(C₂H₄OH), 5-C₂H₅ analogue with CH(CH₃)-CH₂-C(CH₃)₂-N(CH₃)(C₂H₄OH)] | 719 |
| 62 | H | H | H | H | SO₂ | [N-ethyl, 5-OCH₃ analogue with CH(CH₃)-CH₂-C(CH₃)₂-N(CH₃)(C₂H₅)] | 660 |
| 63 | H | H | Cl | H | SO₂ | [N,N-dimethyl, 4-methyl analogue with CH(CH₃)-CH₂-C(CH₃)₂-N(CH₃)₂] | 680 |

TABLE 1-continued
General formula: 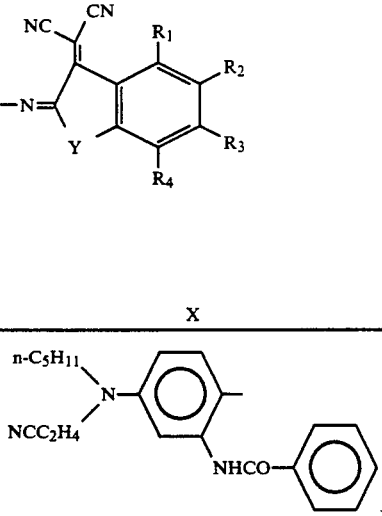
| No. | R₁ | R₂ | R₃ | R₄ | Y | X | Absorption maximum wavelength in acetone (nm) |
|---|---|---|---|---|---|---|---|
| 64 | H | H | Br | H | SO₂ | 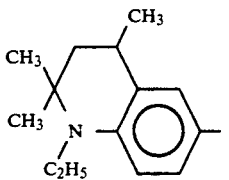 | 707 |
| 65 | H | H | NO₂ | H | SO₂ | 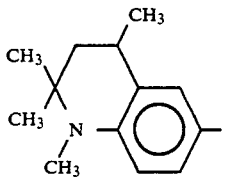 | 730 |
| 66 | H | H | NO₂ | H | SO₂ | 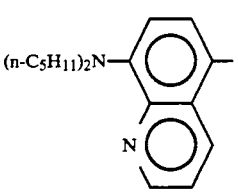 | 729 |
| 67 | H | H | NO₂ | H | SO₂ | 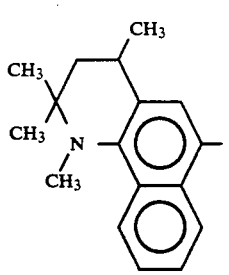 | 715 |
| 68 | H | H | NO₂ | H | SO₂ | 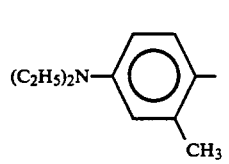 | 730 |
| 69 | H | H | H | Cl | SO₂ | 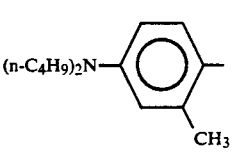 | 725 |
| 70 | H | H | H | Cl | SO₂ | (n-C₄H₉)₂N-C₆H₃(CH₃)- | 726 |

TABLE 1-continued

General formula:

| No. | R₁ | R₂ | R₃ | R₄ | Y | X | Absorption maximum wavelength in acetone (nm) |
|---|---|---|---|---|---|---|---|
| 71 | H | H | H | Cl | SO$_2$ | (structure with CH$_3$, C$_2$H$_5$, N, phenyl with CH$_3$ groups) | 728 |
| 72 | H | H | H | Cl | SO$_2$ | (structure with CH$_3$, C$_4$H$_9$(n), N, phenyl with CH$_3$ groups) | 728 |
| 73 | H | H | OCH$_3$ | H | SO$_2$ | (n-C$_5$H$_{11}$)$_2$N—phenyl—CH$_3$ | 682 |
| 74 | H | H | NHCOCH$_3$ | H | SO$_2$ | (n-C$_5$H$_{11}$)$_2$N—naphthyl | 642 |

EXAMPLE 75

1.50 g of 1,3-bisdicyanovinylindane and 2.50 g of the compound of formula (7):

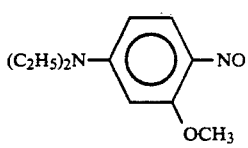

were mixed in 40 ml of acetic anhydride and stirred at 20°~25° C. for 5 hours. The mixed solution was filtered, washed with ice-cold methanol and dried. The resulting product was recrystallized from chloroform to give 1.80 g of purified cakes of the compound of the following formula (8). Yield: 67.3%; melting point; above 300° C.

Absorbance in acetone: λmax=710 nm, ε=3.95×10$^4$.

(8)

(C$_2$H$_5$)$_2$N—phenyl(OCH$_3$)—N=indane with NC/CN groups

EXAMPLE 76

1.50 g of 1,3-bisdicyanovinylidane and 3.81 g of the compound of formula (9):

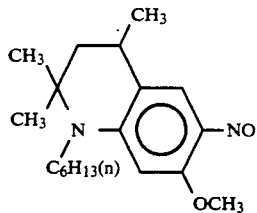

(9)

were mixed in 40 ml of acetic anhydride and stirred at 21°~25° C. for 8 hours. The mixed solution was filtered, washed with ice-cold methanol and dried. The resulting product was recrystallized from chloroform to give 2.06 g of purified cakes of the compound of the following formula (10). Yield: 63.2%; melting point: 247°~249° C.

Absorbance in acetone solution: $\lambda max = 715$ nm, $\epsilon = 4.61 \times 10^4$.

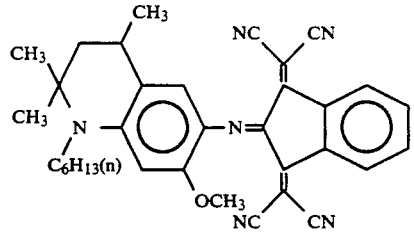

(10)

EXAMPLES 77-119

The compounds shown in Table 2 below were produced in the same way as Example 75 or Example 76.

TABLE 2

General formula: 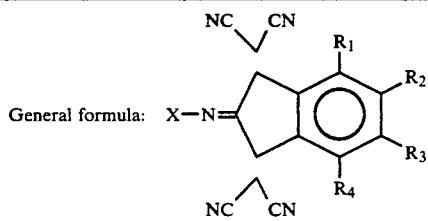

| No. | R₁ | R₂ | R₃ | R₄ | X | Absorption maximum wavelength in acetone (nm) |
|---|---|---|---|---|---|---|
| 77 | H | H | H | H | ![phenyl with N(C₂H₄OH)₂ and OC₂H₄OH] | 711 |
| 78 | H | H | H | H | ![phenyl with N(n-C₆H₁₃)₂ and OCH₃] | 709 |
| 79 | H | H | H | H | ![phenyl with N(C₂H₄Br)₂ and OCH₃] | 712 |
| 80 | H | H | H | H | ![phenyl with N(C₂H₅)(C₂H₄CN) and OCH₃] | 711 |
| 81 | H | H | H | H | ![phenyl with NH-phenyl and OH] | 712 |

TABLE 2-continued
General formula: 
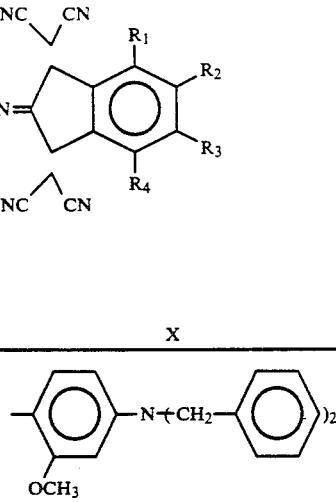
| No. | R₁ | R₂ | R₃ | R₄ | X | Absorption maximum wavelength in acetone (nm) |
|-----|----|----|----|----|---|-----------------------------------------------|
| 82 | H | H | H | H | 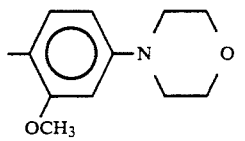 | 710 |
| 83 | H | H | H | H | 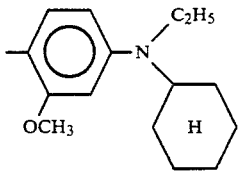 | 708 |
| 84 | H | H | H | H | 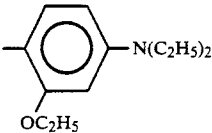 | 710 |
| 85 | H | H | H | H | 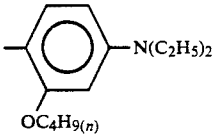 | 710 |
| 86 | H | H | H | H | 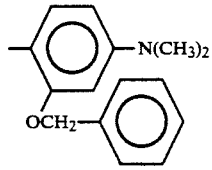 | 711 |
| 87 | H | H | H | H | 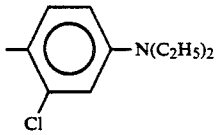 | 711 |
| 88 | H | H | H | H | 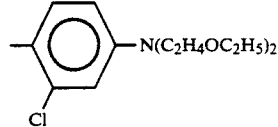 | 701 |
| 89 | H | H | H | H | | 703 |

TABLE 2-continued
General formula: 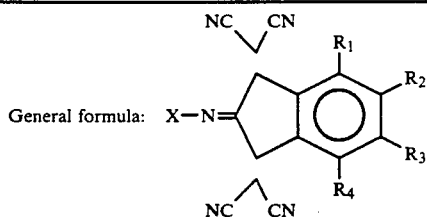
| No. | R₁ | R₂ | R₃ | R₄ | X | Absorption maximum wavelength in acetone (nm) |
|---|---|---|---|---|---|---|
| 90 | H | H | H | H | 4-[N(C₂H₄COOCH₃)₂]-3-Br-phenyl | 702 |
| 91 | H | H | H | H | 4-[N(C₂H₄OCOCH₃)₂]-3-Br-phenyl | 703 |
| 92 | H | H | H | H | 4-[N(C₂H₅)(C₂H₄O-phenyl)]-3-I-phenyl | 704 |
| 93 | H | H | H | H | 2,5-di-OCH₃-4-N(C₂H₅)₂-phenyl | 715 |
| 94 | H | H | H | H | 2-CH₃-5-OCH₃-4-N(C₂H₅)₂-phenyl | 712 |
| 95 | H | H | H | H | 2-Cl-4-N(C₂H₅)₂-5-OCOCH₃-phenyl | 710 |
| 96 | H | H | H | H | 2-CH(CH₃)CH₂C(CH₃)₂-, N(CH₃)(C₂H₅), 5-OCH₃-phenyl | 715 |

TABLE 2-continued

General formula:

$$X-N=\text{[indane with R}_1, R_2, R_3, R_4\text{ and two C(CN)}_2\text{ groups]}$$

| No. | R₁ | R₂ | R₃ | R₄ | X | Absorption maximum wavelength in acetone (nm) |
|---|---|---|---|---|---|---|
| 97 | H | H | H | H | [2-OCH₃, 5-CH₃-phenyl]-N(C₈H₁₇(n))-C(CH₃)₂-CH₂-CH(CH₃)- | 714 |
| 98 | H | H | H | H | [2-OCH₃, 5-CH₃-phenyl]-N(CH₂CH=CH₂)-C(CH₃)₂-CH₂-CH(CH₃)- | 713 |
| 99 | H | H | H | H | [2-OC₂H₄OH, 5-CH₃-phenyl]-N(C₂H₄OH)-C(CH₃)₂-CH₂-CH(CH₃)- | 714 |
| 100 | H | H | H | H | [2-OC₂H₅, 5-CH₃-phenyl]-N(C₂H₅)-C(CH₃)₂-CH₂-CH(CH₃)- | 715 |
| 101 | H | H | H | H | [2-Cl, 5-CH₃-phenyl]-N(C₂H₅)-C(CH₃)₂-CH₂-CH(CH₃)- | 705 |
| 102 | H | H | H | H | [2-Br, 5-CH₃-phenyl]-N(C₂H₅)-C(CH₃)₂-CH₂-CH(CH₃)- | 706 |

TABLE 2-continued

General formula:

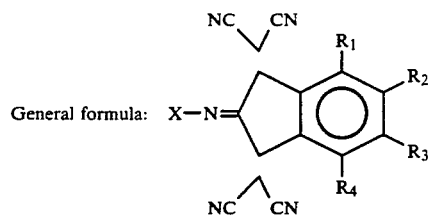

| No. | R₁ | R₂ | R₃ | R₄ | X | Absorption maximum wavelength in acetone (nm) |
|---|---|---|---|---|---|---|
| 103 | H | H | H | H | ![structure] 5-methyl-8-N(C₂H₅)₂ quinoline | 713 |
| 104 | H | H | H | H | ![structure] 5-methyl-2-methyl-8-N(C₂H₅)₂ quinoline | 715 |
| 105 | Cl | H | H | H | ![structure] substituted phenyl with CH₃, OCH₃, and N(CH(CH₃)C(CH₃)₂-)(C₂H₅) | 720 |
| 106 | Cl | H | H | H | ![structure] phenyl with CH₃, OCH₃, N(C₂H₅)₂ | 716 |
| 107 | Br | H | H | H | ![structure] phenyl with CH₃, OCH₃, N(n-C₄H₉)₂ | 716 |
| 108 | I | H | H | H | ![structure] substituted phenyl with CH₃, OCH₃, and N(CH(CH₃)C(CH₃)₂-)(C₂H₅) | 717 |

TABLE 2-continued

General formula:

$$X-N=\text{(indene with } R_1, R_2, R_3, R_4 \text{ and two } C(CN)_2 \text{ groups)}$$

| No. | $R_1$ | $R_2$ | $R_3$ | $R_4$ | X | Absorption maximum wavelength in acetone (nm) |
|---|---|---|---|---|---|---|
| 109 | $NO_2$ | H | H | H | 3-Cl-4-CH₃-phenyl-$N(C_2H_5)_2$ | 720 |
| 110 | H | CN | H | H | 3-$OCH_3$-4-CH₃-phenyl-$N(n\text{-}C_4H_9)_2$ | 719 |
| 111 | $COOCH_3$ | H | H | H | 3-$OCOCH_3$-4-CH₃-phenyl-$N(C_2H_5)_2$ | 720 |
| 112 | $CON(CH_3)_2$ | H | H | H | 2-(1,1,3-trimethyl... )-4-CH₃-5-$OCH_3$-phenyl-$N(CH_3)(C_2H_5)$ derivative | 721 |
| 113 | H | OH | H | H | 3-$OC_2H_5$-4-CH₃-phenyl-$N(C_2H_5)_2$ | 705 |
| 114 | H | $OCH_3$ | H | H | 3-$OC_4H_{9(n)}$-4-CH₃-phenyl-$N(C_2H_5)_2$ | 700 |
| 115 | H | $OCOCH_3$ | H | H | 2-(1,1,3-trimethyl... )-4-CH₃-5-$OCH_3$-phenyl-$N(CH_3)(C_4H_{9(n)})$ derivative | 703 |

TABLE 2-continued

General formula:

$$X-N=\underset{NC\diagdown CN}{\overset{NC\diagdown CN}{\text{indane}}}\begin{matrix}R_1\\R_2\\R_3\\R_4\end{matrix}$$

| No. | $R_1$ | $R_2$ | $R_3$ | $R_4$ | X | Absorption maximum wavelength in acetone (nm) |
|---|---|---|---|---|---|---|
| 116 | H | OCOO—C$_6$H$_5$ | H | H | —C$_6$H$_3$(OCH$_3$)—N(n-C$_4$H$_9$)$_2$ | 702 |
| 117 | N(CH$_3$)$_2$ | H | H | H | —C$_6$H$_3$(OC$_2$H$_5$)—N(C$_2$H$_4$Br)$_2$ | 691 |
| 118 | CF$_3$ | H | H | H | —C$_6$H$_3$(OC$_2$H$_4$OH)—N(C(CH$_3$)$_2$CH$_3$)(C$_2$H$_4$OH) (with CH$_3$ branch) | 706 |
| 119 | CH$_3$ | H | H | H | —C$_6$H$_3$(OCH$_3$)—N(C$_2$H$_5$)$_2$ | 707 |

EXAMPLE 120

Figure 5:
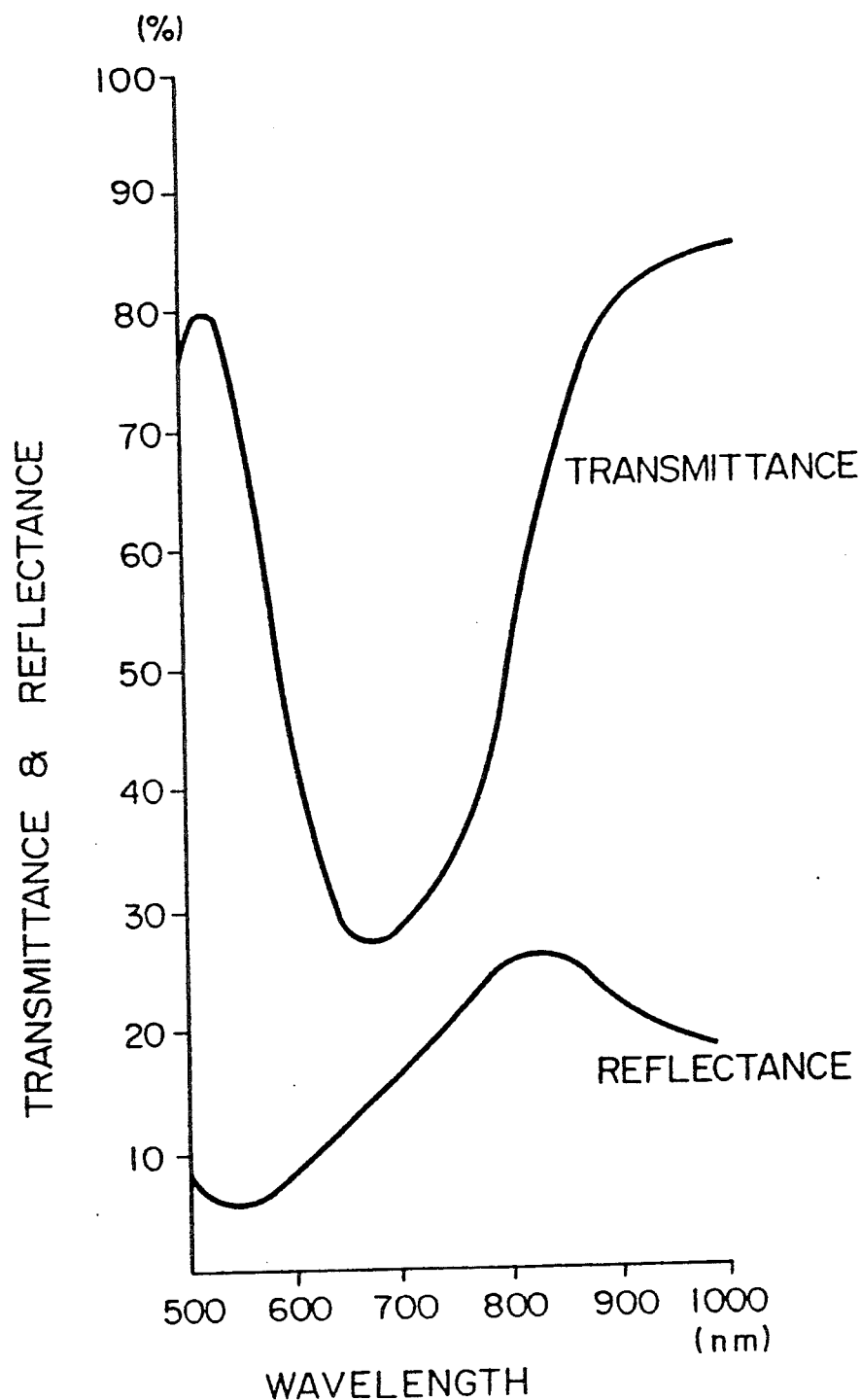
FIG. 5 shows the transmittance and reflectance spectra of the recording medium obtained in Example 120.

A trichloroethylene solution of the compound obtained in Example 1 was spin-coated on a glass substrate at 4,000 r.p.m. for 20 seconds to form a 600 Å thick recording layer on said substrate to make an optical information recording medium. The transmittance and reflectance curves of the obtained recording medium are shown in FIG. 5.

When this recording medium was irradiated with semiconductor laser of 780 nm in oscillation wavelength at 40 mJ/cm$^2$ with a spot diameter of 1 μm, there was observed formation of a clear spot.

EXAMPLE 121

Figure 6:
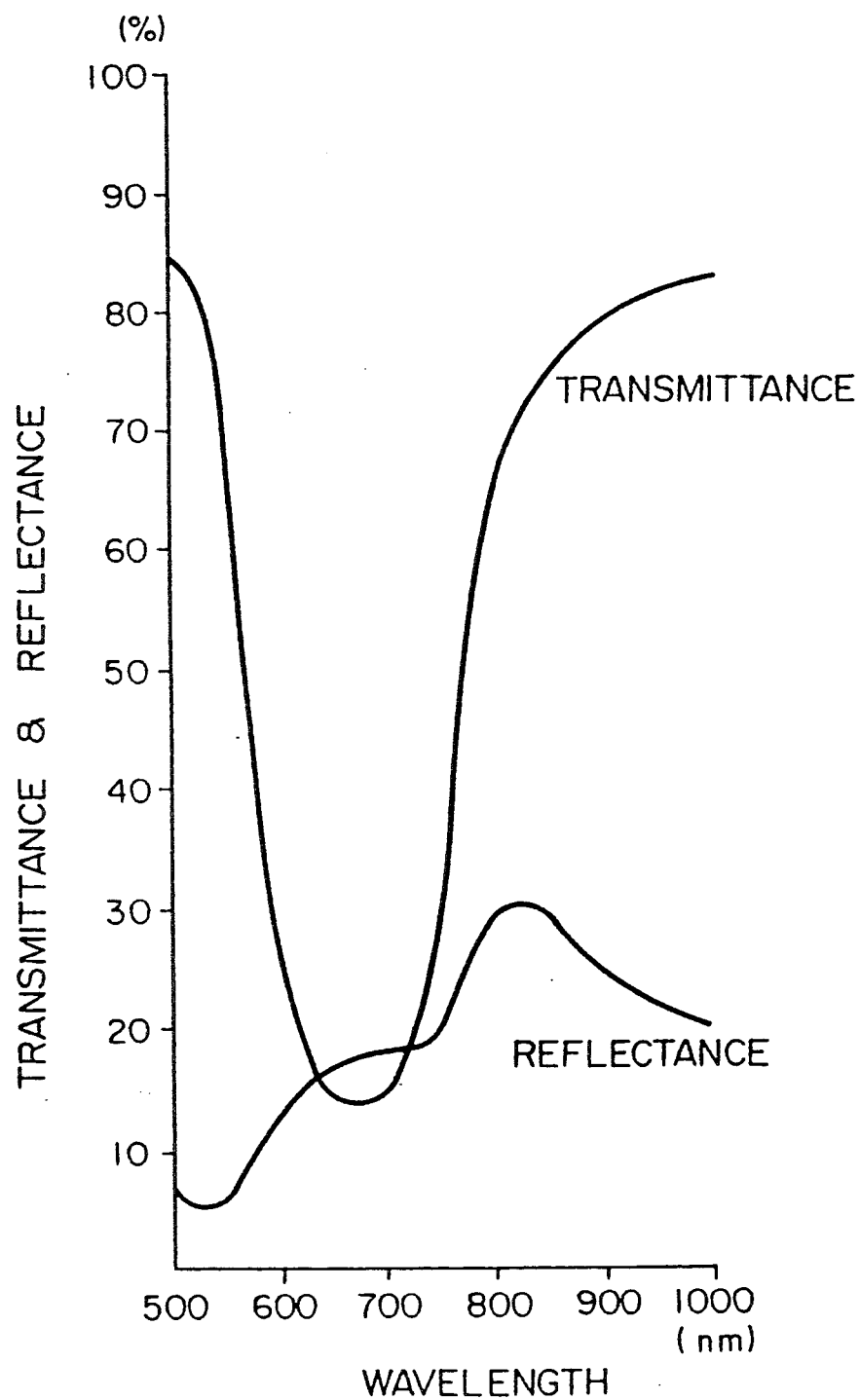
FIG. 6 shows the transmittance and reflectance spectra of the recording medium obtained in Example 121.

A chloroform solution of the compound obtained in Example 2 was spin-coated on a glass substrate at 4,000 r.p.m. for 20 seconds to form a 600 Å thick recording layer on said substrate to make an optical information recording medium. The transmittance and reflectance curves of this recording medium are shown in FIG. 6.

When this recording medium was irradiated with semiconductor laser of 780 nm in oscillation wavelength at 40 mJ/cm$^2$ with a spot diameter of 1 μm, there was observed formation of a clear spot.

EXAMPLE 122

Figure 7:
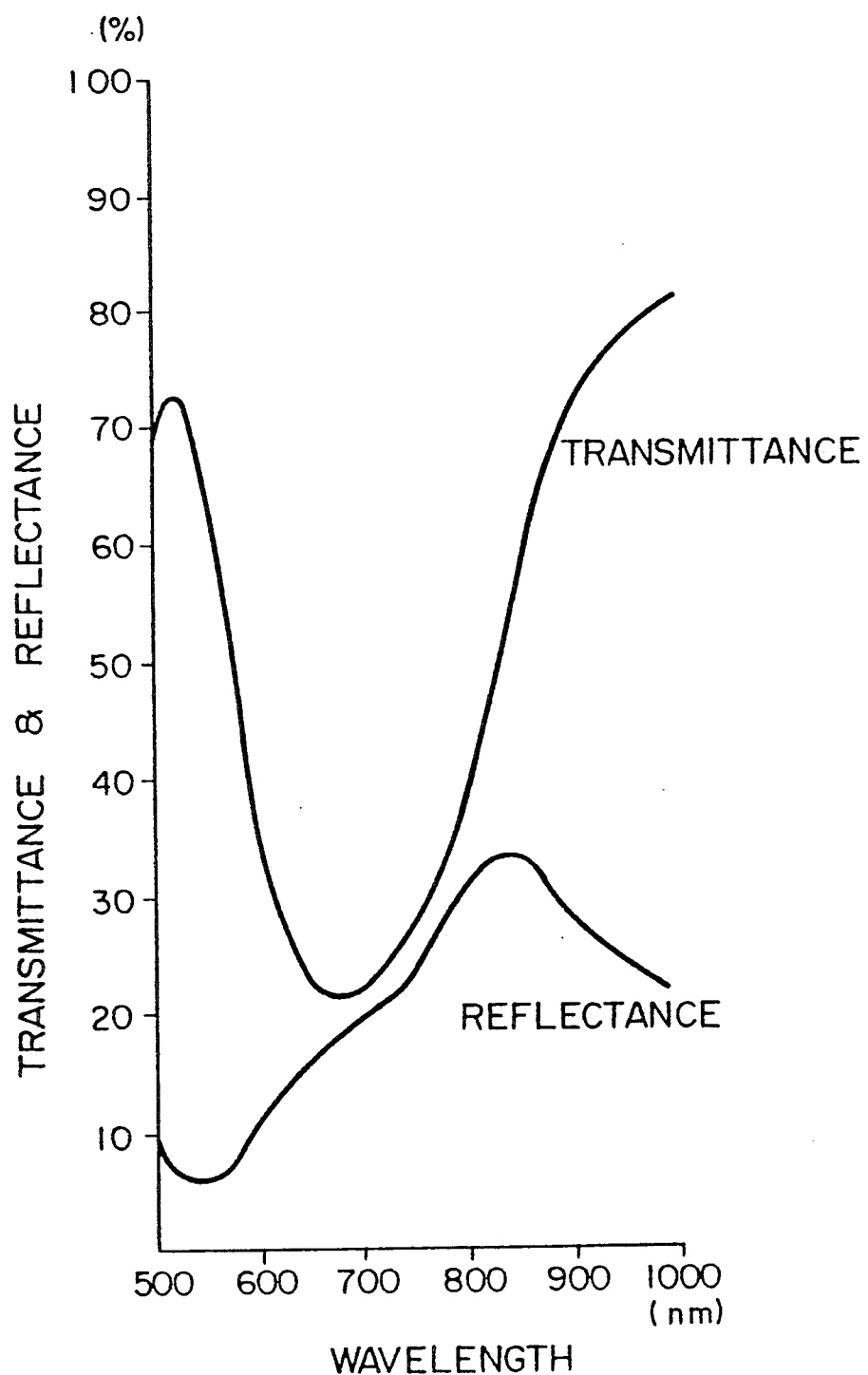
FIG. 7 shows the transmittance and reflectance spectra of the recording medium obtained in Example 122.

A chloroform solution of the compound obtained in Example 3 was spin-coated on a glass substrate at 2,000 r.p.m. for 20 seconds to form a 800 Å thick recording layer on said substrate to make an optical information recording medium. The transmittance and reflectance curves of the obtained recording medium are shown in FIG. 7.

When this recording medium was irradiated with semiconductor laser of 780 nm in oscillation wavelength at 40 mJ/cm$^2$ with a spot diameter of 1 μm, formation of a clear spot was observed.

EXAMPLE 123

The dye used in Example 122 was vacuum deposited on a PMMA substrate to form a 800 Å thick recording layer on said substrate to make a recording medium. Said vacuum deposition was carried out at a degree of vacuum below 3×10$^{-5}$ Torr, a resistance heating boat temperature of 185°~195° C. and a deposition rate of about 0.5 Å/sec. The obtained recording medium showed the similar transmittance and reflectance spectra to Example 122.

When this recording medium was irradiated with semiconductor laser of 780 nm in oscillation wavelength at 40 mJ/cm$^2$ with a spot diameter of 1 μm, formation of a clear spot was observed.

EXAMPLE 124

Figure 8:
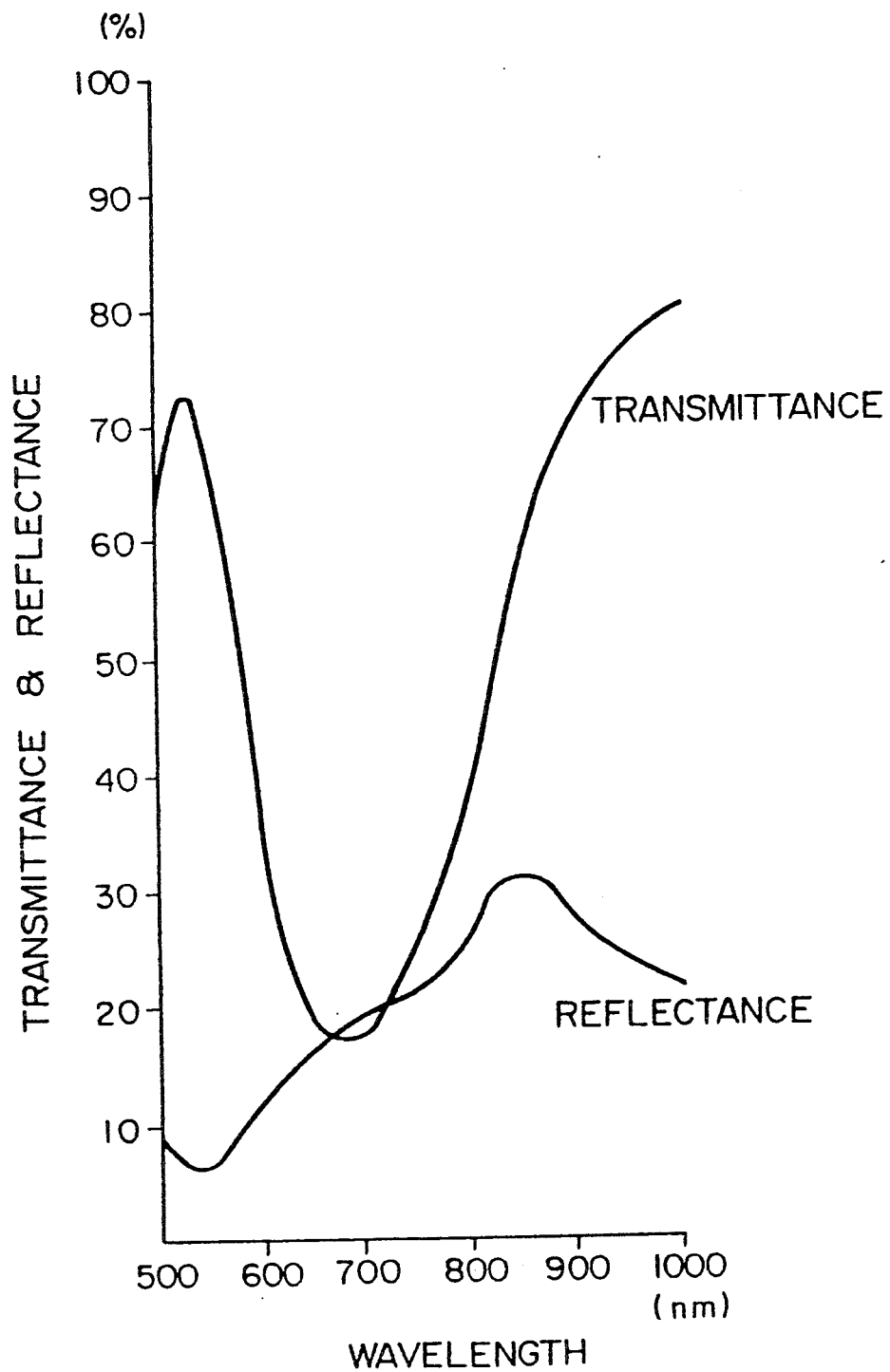
FIG. 8 shows the transmittance and reflectance spectra of the recording medium obtained in Example 124.

A tetrachloroethylene solution of the compound obtained in Example 17 was spin-coated on a glass substrate at 2,000 r.p.m. for 20 seconds to form a 700 Å thick recording layer on said substrate to make an optical information recording medium. The transmittance and reflectance curves of the obtained recording medium are shown in FIG. 8.

When this recording medium was irradiated with semiconductor laser of 780 nm in oscillation wavelength at 40 mJ/cm$^2$ with a spot diameter of 1 μm, there was admitted formation of a clear spot.

EXAMPLE 125

The dye used in Example 124 was vacuum deposited on a PMMA substrate to form a 700 Å thick recording layer on said substrate to make an optical information recording medium. Vacuum deposition was carried out at a degree of vacuum below $3 \times 10^{-5}$ Torr, a resistance heating boat temperature of 195°~205° C. and a deposition rate of about 0.5 Å/sec. The obtained recording medium showed the similar transmittance and reflectance spectra to Example 124.

When this recording medium was irradiated with semiconductor laser of 780 nm in oscillation wavelength at 40 mJ/cm$^2$ with a spot diameter of 1 μm, there was observed formation of a clear spot.

EXAMPLE 126

Figure 9:
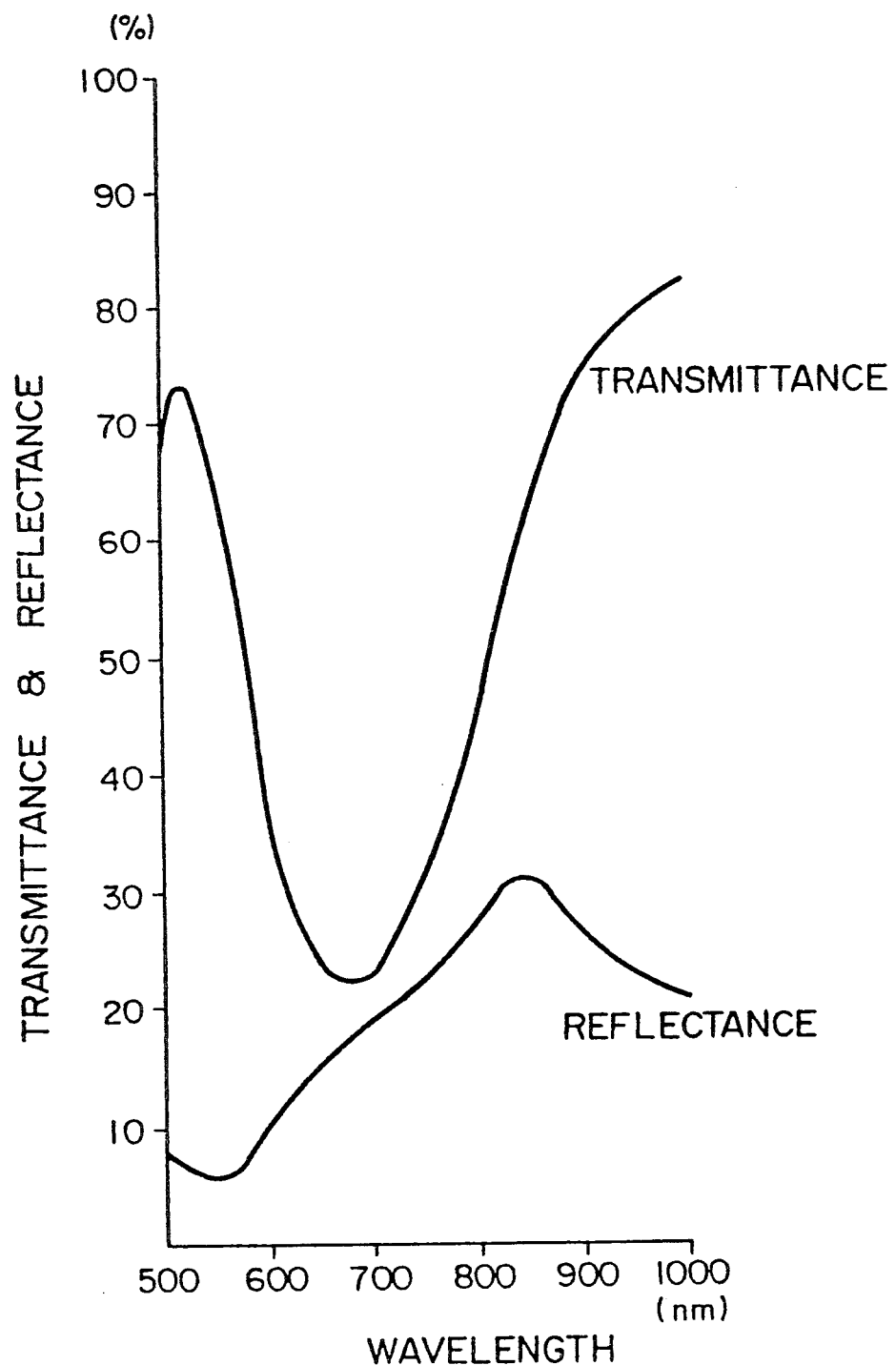
FIG. 9 shows the transmittance and reflectance curves of the recording medium obtained in Example 126.

A chloroform solution of the compound obtained in Example 31 was spin-coated on a glass substrate at 2,000 r.p.m. for 20 seconds to form a 700 Å thick recording layer on said substrate to make an optical information recording medium. The transmittance and reflectance curves of the obtained recording medium are shown in FIG. 9.

When this recording medium was irradiated with semiconductor laser of 780 nm in oscillation wavelength at 40 mJ/cm$^2$ with a spot diameter of 1 μm, there was observed formation of a clear spot.

EXAMPLE 127

The dye used in Example 126 was vacuum deposited on a PMMA substrate to form a 700 Å thick recording layer on said substrate to make an optical information recording medium. Vacuum deposition was carried out at a degree of vacuum below $3 \times 10^{-5}$ Torr, a resistance heating boat temperature of 180°~190° C. and a deposition rate of about 0.5 Å/sec. The obtained recording medium showed the similar transmittance and reflectance spectra to Example 124.

When this recording medium was irradiated with semiconductor laser of 780 nm in oscillation wavelength at 40 mJ/cm$^2$ with a spot diameter of 1 μm, there was observed formation of a clear spot.

EXAMPLE 128

Figure 10:
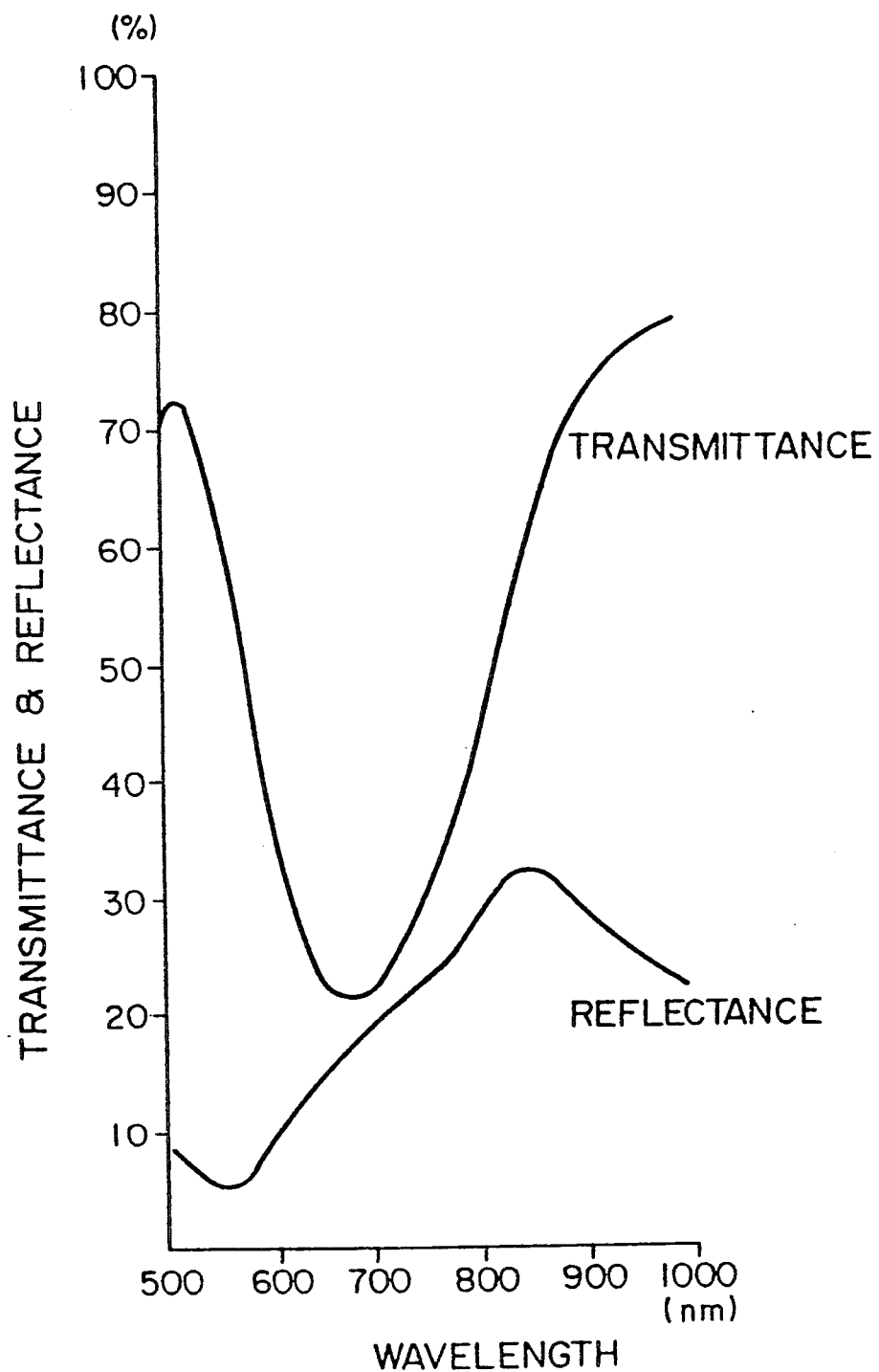
FIG. 10 shows the transmittance and reflectance curves of the recording medium obtained in Example 128.

A chloroform solution of a 1:1 (by weight) mixture of the compound obtained in Example 17 and the compound obtained in Example 31 was spin-coated on a glass substrate at 2,000 r.p.m. for 20 seconds to form a 700 Å thick recording layer on said substrate to make an optical information recording medium. The transmittance and reflectance curves of the obtained recording medium are shown in FIG. 10.

When this recording medium was irradiated with semiconductor laser of 780 nm in oscillation wavelength at 40 mJ/cm$^2$ with a spot diameter of 1 μm, there was observed formation of a clear spot.

EXAMPLE 129

Figure 11:
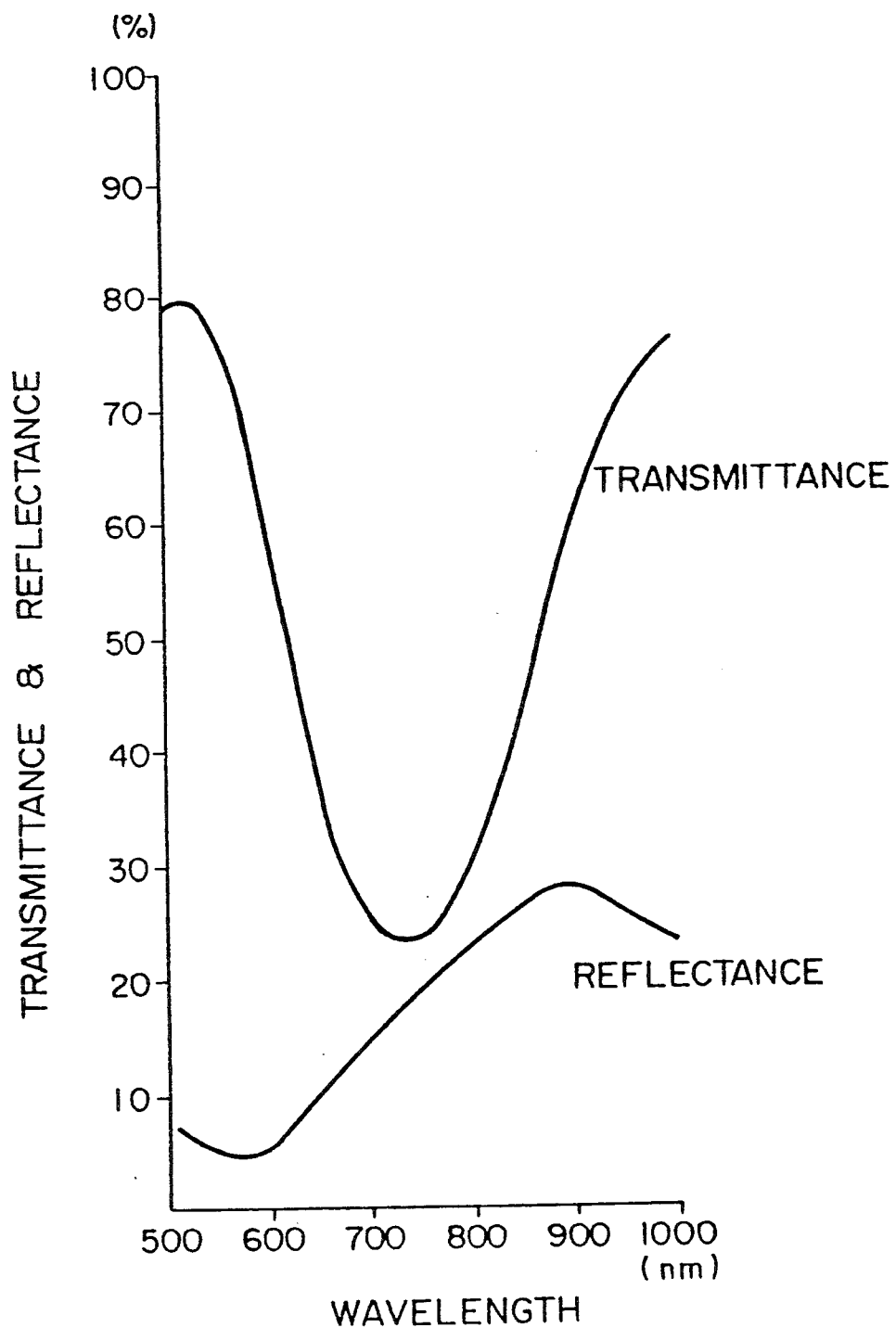
FIG. 11 shows the transmittance and reflectance curves of the recording medium obtained in Example 129.

A trichloroethylene solution of the compound obtained in Example 75 was spin-coated on a glass substrate at 2,000 r.p.m. for 20 seconds to form an 800 Å thick recording layer on said substrate to make an optical information recording medium. The transmittance and reflectance curves of the obtained recording medium are shown in FIG. 11.

When this recording medium was irradiated with semiconductor laser of 830 nm in oscillation wavelength at 40 mJ/cm$^2$ with a spot diameter of 1 μm, there was observed formation of a clear spot.

EXAMPLE 130

Figure 12:
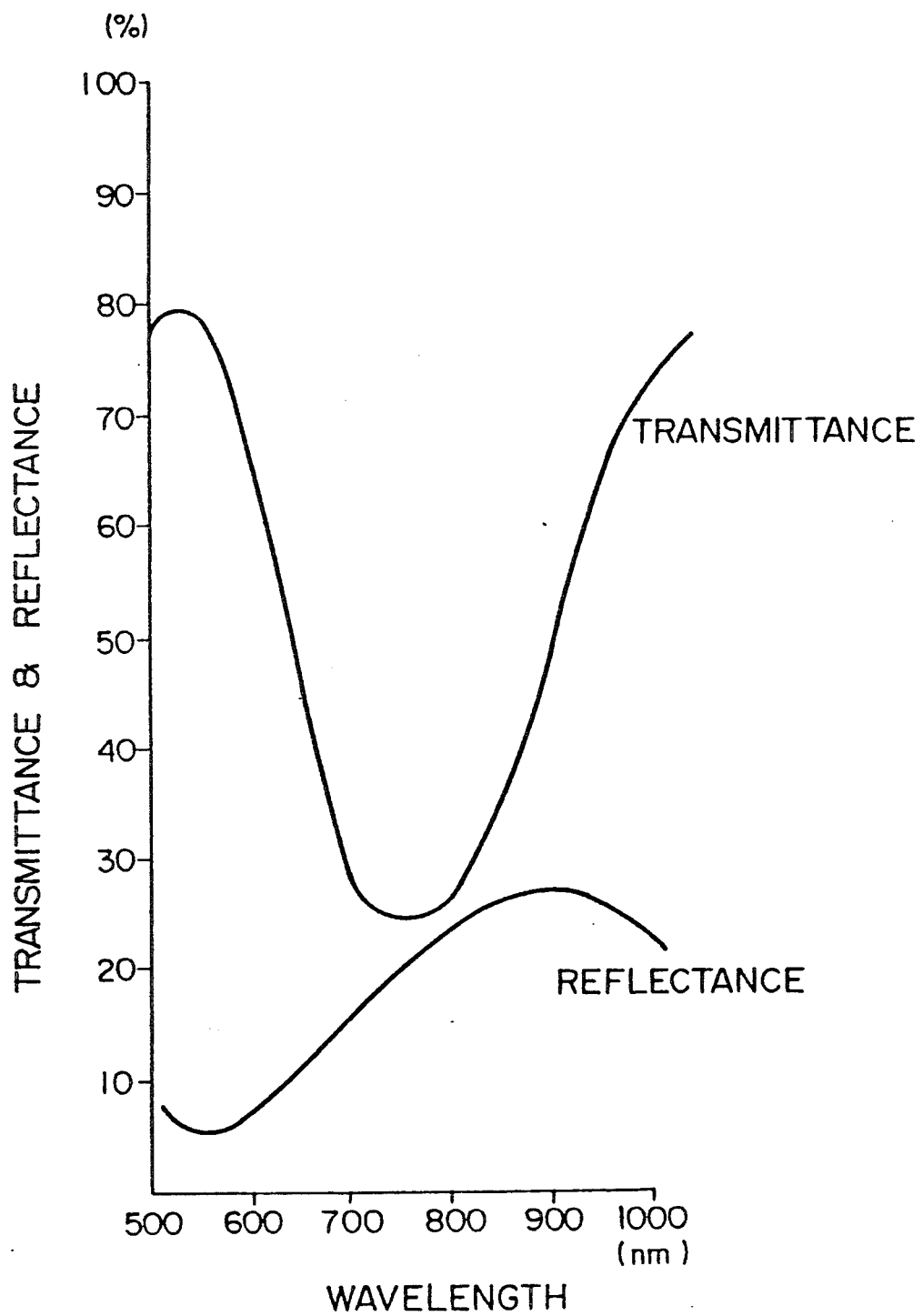
FIG. 12 shows the transmittance and reflectance curves of the recording medium obtained in Example 130.

A chloroform solution of the compound obtained in Example 76 was spin-coated on a glass substrate at 2,000 r.p.m. for 20 seconds to form a 700 Å thick recording layer on said substrate to make an optical information recording medium. The transmittance and reflectance curves of the obtained recording medium are shown in FIG. 12.

When this recording medium was irradiated with semiconductor laser of 830 nm in oscillation wavelength at 40 mJ/cm$^2$ with a spot diameter of 1 μm, there was observed formation of a clear spot.

COMPARATIVE EXAMPLE 1

Figure 13:
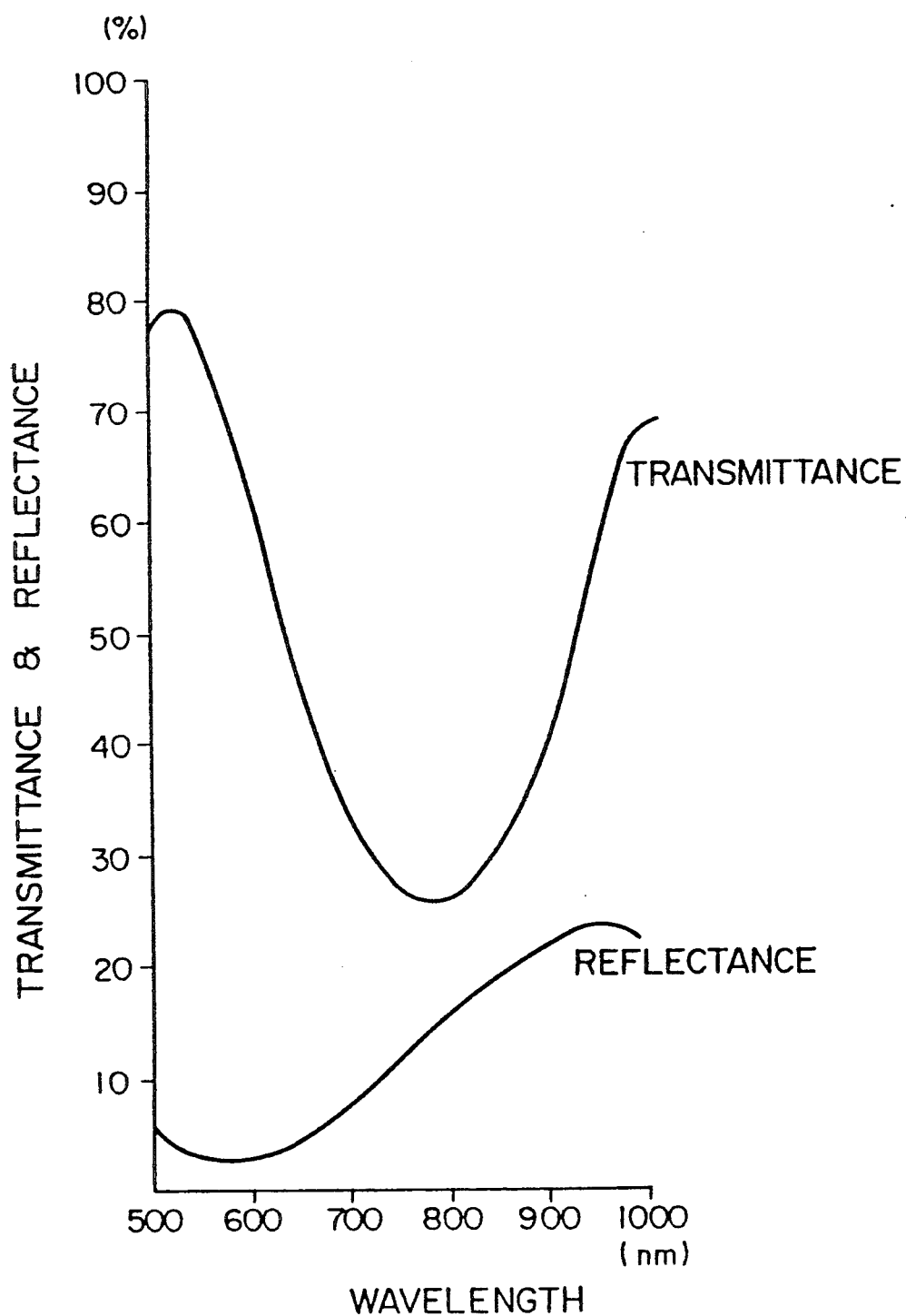
FIG. 13 shows the transmittance and reflectance curves of the recording medium obtained in Comparative Example 1.

A chloroform solution of the compound of the following structural formula was spin-coated on a glass substrate at 2,000 r.p.m. for 20 seconds to form a 700 Å thick recording layer on said substrate to make an optical information recording medium. The transmittance and reflectance curves of the obtained recording medium are shown in FIG. 13. As seen from FIG. 13, this recording medium shows no high reflectance in the oscillation wavelength region of semiconductor laser.

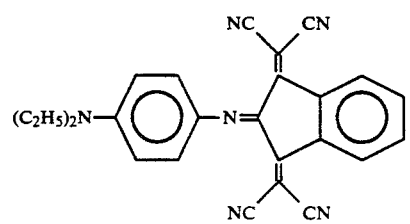

What is claimed is:

1. Azamethine compounds represented by formula (I):

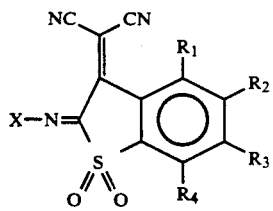

wherein X represents

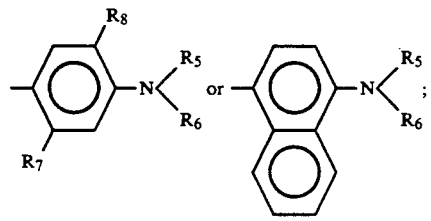

$R_1$ to $R_4$ represent independently a hydrogen atom, an alkyl group, an alkoxyl group, a halogen atom, a nitro group, a cyano group, a hydroxyl group, an amino group which may be substituted by —COR, —A—R or

$R_5$ and $R_6$ represent independently a hydrogen atom or an alkyl group which may be substituted by a cyano, hydroxyl, alkoxyl group or —OCOR; $R_7$ and $R_8$ represent independently a hydrogen atom, an alkyl group, an alkoxyl group, a hydroxyl group, a halogen atom, a nitro group, a cyano group, —NHSO$_2$CH$_3$, —A—R or $$-E\diagup^{R}_{R'} \quad , \quad (I)$$

wherein —A represents $$-NHC-, -NHCO-, -C-, -OC-, \atop \underset{O}{\|} \quad \underset{O}{\|} \quad \underset{O}{\|} \quad \underset{O}{\|}$$

$$-OCO- \text{ or } -CO-, -E\diagup \atop \underset{O}{\|} \quad \underset{O}{\|} \quad \diagdown$$

$$-NHCN\diagup \text{ or } -C-N\diagup , \atop \underset{O}{\|} \diagdown \quad \underset{O}{\|} \diagdown$$

and R and R' represent independently a hydrogen atom, an alkyl group or a phenyl group.

2. The azamethine compounds according to claim 1, wherein in the formula (I) X represents

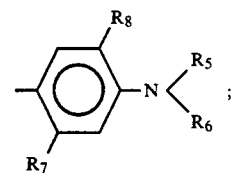

$R_5$ and $R_6$ represent independently a hydrogen atom or an alkyl group; $R_7$ represents an alkyl group, an alkoxyl group, a hydroxyl group, a halogen atom or $$-OC-R'' \atop \underset{O}{\|}$$

wherein R" represents an alkyl group; $R_8$ represents a hydrogen atom, an alkyl group, an alkoxyl group or a halogen atom.

3. The azamethine compounds according to claim 2, wherein in the formula (I) $R_7$ represents an alkyl group or an alkoxyl group.

* * * * *

UNITED STATES PATENT AND TRADEMARK OFFICE
CERTIFICATE OF CORRECTION

PATENT NO. : 5,136,054
DATED : August 4, 1992
INVENTOR(S) : Takeshi HIOKI et al

It is certified that error appears in the above-identified patent and that said Letters Patent is hereby corrected as shown below:

Column 52, line 15, --represents-- should appear after " $-E\genfrac{}{}{0pt}{}{\nearrow}{\searrow}$ ".

Signed and Sealed this

Twenty-third Day of November, 1993

Attest:

BRUCE LEHMAN

*Attesting Officer*      *Commissioner of Patents and Trademarks*